(12) United States Patent
Fontayne et al.

(10) Patent No.: US 6,540,656 B2
(45) Date of Patent: Apr. 1, 2003

(54) TARGETING FIXTURE FOR A GRID TEMPLATE

(75) Inventors: Diego Y. Fontayne, Montebello, NY (US); Scott D. Salmon, Hoboken, NJ (US); Christopher J. Claypool, Orlando, FL (US)

(73) Assignee: Integrated Implant Systems LLC, Arlington, VA (US)

( * ) Notice: Subject to any disclaimer, the term of this patent is extended or adjusted under 35 U.S.C. 154(b) by 0 days.

(21) Appl. No.: 09/858,656

(22) Filed: May 17, 2001

(65) Prior Publication Data

US 2002/0038071 A1 Mar. 28, 2002

Related U.S. Application Data

(60) Provisional application No. 60/205,054, filed on May 18, 2000.

(51) Int. Cl.$^7$ ................................................. A61N 5/00
(52) U.S. Cl. ............................................... 600/7; 600/8
(58) Field of Search ........................................ 600/7, 8

(56) References Cited

U.S. PATENT DOCUMENTS

| | | | |
|---|---|---|---|
| 3,704,707 A | 12/1972 | Halloran | |
| 4,267,149 A | 5/1981 | Bruckner et al. | |
| 4,400,170 A | 8/1983 | McNaughton et al. | |
| 4,451,254 A | 5/1984 | Dinius et al. | |
| 4,700,692 A | 10/1987 | Baumgartner | |
| 4,838,265 A | 6/1989 | Cosman et al. | |
| 5,242,373 A | 9/1993 | Scott et al. | |
| 5,305,203 A | 4/1994 | Raab | |
| 5,366,896 A | 11/1994 | Margrey et al. | |
| 5,514,101 A | 5/1996 | Schultz et al. | |
| 5,609,152 A | 3/1997 | Pellegrino | |
| 5,860,909 A | 1/1999 | Mick et al. | |
| 5,871,448 A | 2/1999 | Ellard ........................ 600/459 |
| 5,938,583 A | 8/1999 | Grimm .......................... 600/7 |
| 6,002,859 A | 12/1999 | DiGioia, III et al. | |
| 6,007,474 A | 12/1999 | Rydell | |
| 6,102,844 A | 8/2000 | Ravins et al. | |
| 6,129,670 A | 10/2000 | Burdette et al. | |
| 6,132,358 A | 10/2000 | Glenn et al. | |
| 6,206,832 B1 | 3/2001 | Downey et al. | |
| 6,214,013 B1 | 4/2001 | Lambrecht et al. | |
| 6,267,718 B1 | 7/2001 | Vitali et al. | |
| 6,270,472 B1 | 8/2001 | Antaki et al. | |
| 6,387,034 B1 | 5/2002 | Lee | |
| 6,432,035 B1 | 8/2002 | Ravins et al. | |

FOREIGN PATENT DOCUMENTS

WO     97/22379     6/1997

*Primary Examiner*—Gerald A. Michalsky
(74) *Attorney, Agent, or Firm*—Heller Ehrman White & McAuliffe, LLP

(57) ABSTRACT

A targeting fixture allows for x-y movement of a targeting fixture with respect to a grid template. The targeting fixture includes a cradle unit, which accepts a seed implanting device. The cradle unit is hingedly connected to a housing surrounding the grid template. The housing is capable of x-y movement by actuation of x-y knobs provided on the housing.

4 Claims, 16 Drawing Sheets

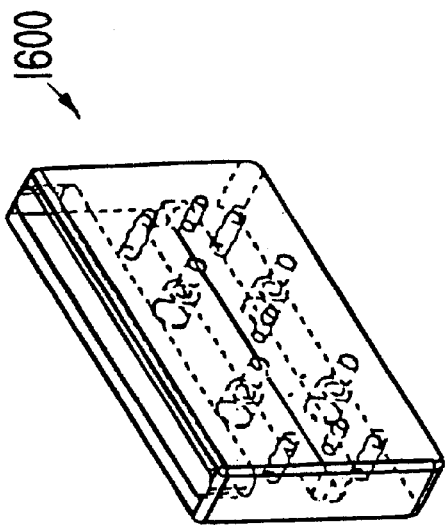
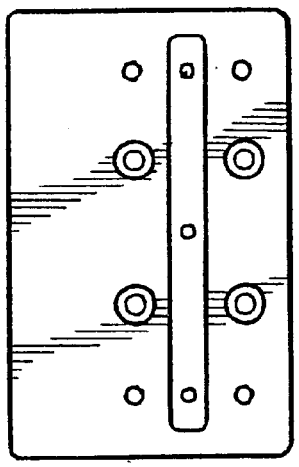
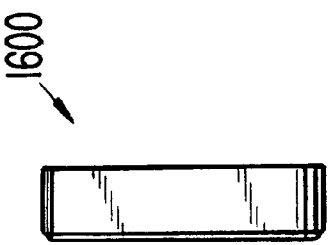
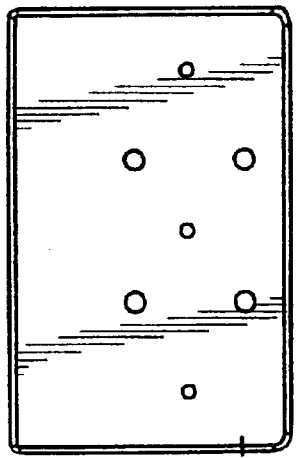

TARGETING FIXTURE FOR A GRID TEMPLATE

RELATED APPLICATIONS

This application claims priority to U.S. provisional application No. 60/205,054, filed May 18, 2000, which is incorporated in its entirety herein by reference.

BACKGROUND OF THE INVENTION

1. Field of the Invention

The present invention relates to a targeting fixture for a grid template. More particularly, the present invention relates to a targeting fixture for providing a seed-implanting instrument in a proper position with respect to a grid template, to thereby apply the seeds in order to treat a patient.

2. Description of the Related Art

For treating prostate cancer, radioactive seeds are provided to various locations within a patient's prostate gland. Typically, a base unit which includes an ultrasound unit is used to determine the exact location of the patient's prostate gland with respect to the base unit. The ultrasound unit includes a probe, which is inserted into the patient's rectum while the patient is lying on his back. A grid template is mounted onto the base unit, whereby the grid template includes a plurality of rows and columns of holes in which a needle can be inserted. Typically, the grid template includes 13 by 13 matrix of needle holes, where adjacent holes on a row or column are 5 mm apart. Every other row is labeled with a number, and every other column is labeled with an alphabetic character. There is a direct relation between the centerline axis of the ultrasound probe and the position of the holes of the grid template. The base unit is capable of moving either inwards or outwards with respect to the patient.

By using the ultrasound unit, a precise position of the proximal and distal positions of the prostate gland can be determined and recorded. The distal position of the prostate gland is also called the "zero retraction point". Once that information is recorded, a pre-plan can be determined by a doctor, where the pre-plan corresponds to a plan for injecting seeds into particular locations within the patient's prostate gland. Such treatment is generally started by placing the needle at the zero retraction point, and then applying seeds with respect to that reference point. After the pre-plan has been determined, a needle is provided through a hole on the grid template, and then inserted into a region within the patient's body in which the prostate gland is located.

For a conventional seed implantation device, a needle is first placed into a particular hole of the grid template, and then the seed implantation device is held in place by a doctor and attached to the needle. The seed implantation device is then used to inject one or more seeds into the patient's body through the needle. When finished with that hole, the seed implantation device is deattached from the needle, and placed aside. Then, the needle is removed from the grid template, and a new needle is positioned at another hole of the grid template, according to the specific pre-plan for treating the patient's prostate gland. One such conventional seed implantation device is called a MICK applicator, and requires the operator to physically reposition the MICK applicator back onto a new needle positioned onto the grid template.

With such a scheme, the instrument may become unsterile when it is placed aside between replacements of needles. Also, there may exist inaccuracies due to the doctor not placing the instrument at the correct seed-implanting position with respect to the grid template (z-axis position) due to the instrument being somewhat unwieldy and hard to hold in place.

SUMMARY OF THE INVENTION

One object of the present invention is to provide a mounting device that mounts to a grid template, and that allows a seed-implanting instrument to be accurately placed back into position for reinserting seeds using a different hole of the grid template than what was previously used during a treatment of the patient.

Another object of the present invention is to provide a mounting device that provides a direct interface, or track, with the seed implanting instrument for coordinated movement along the z-axis (axis orthogonal to the plane of the grid template).

At least one of these objects may be achieved by a targeting fixture for a grid template, which includes a housing that includes an opening within which the grid template is coupled thereto. The targeting fixture also includes a cradle unit that is configured to receive a seed implanting device. The targeting fixture further includes a hinge unit that hingedly connects the cradle unit to the housing. The targeting fixture also includes an x-y movement unit that provides at least one of x-direction and y-direction movement of the cradle unit with respect to the grid template.

BRIEF DESCRIPTION OF THE DRAWINGS

The invention will become more fully apparent from the following detailed description when read in conjunction with the accompanying drawings with like reference numerals indicating corresponding parts throughout, and wherein:

FIGS. 16A–E show different views of an x-axis slide carriage, according to the present invention.

DETAILED DESCRIPTION OF THE PREFERRED EMBODIMENT

Figure 1:
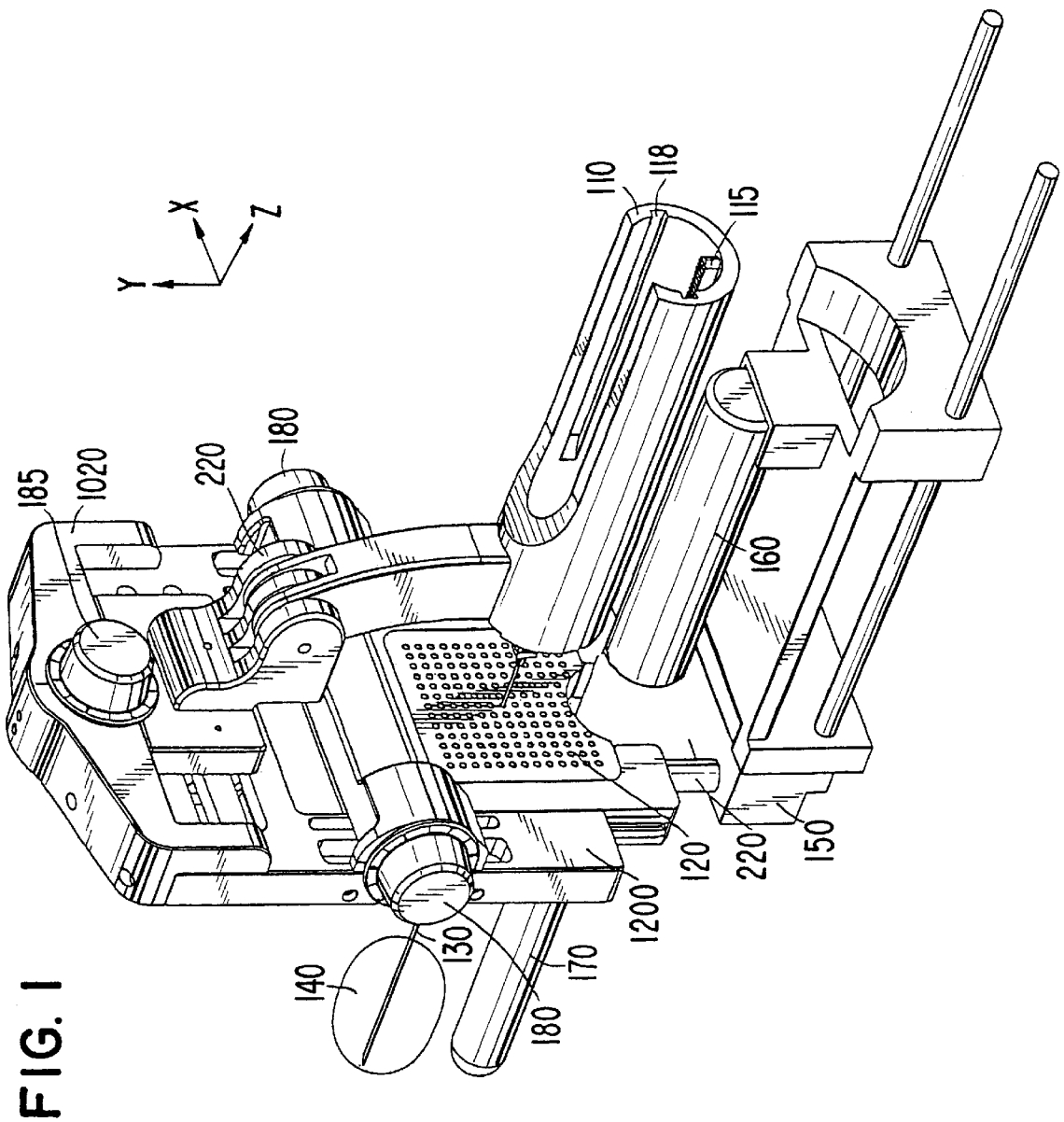
FIG. 1 shows a front perspective view of a targeting fixture attached to a base unit, according to the present invention.

A preferred embodiment of the present invention will be described in detail hereinbelow, with reference to the drawings. In the drawings, preferred dimensions, in inches, are provided by way of explanation of the present invention and not by way of limitation. In other words, the present invention is directed to a particular method and apparatus and equivalents thereof with respect to a targeting fixture for a grid template, and not to the exact sizes of the elements that make up the targeting fixture.

Figure 2:
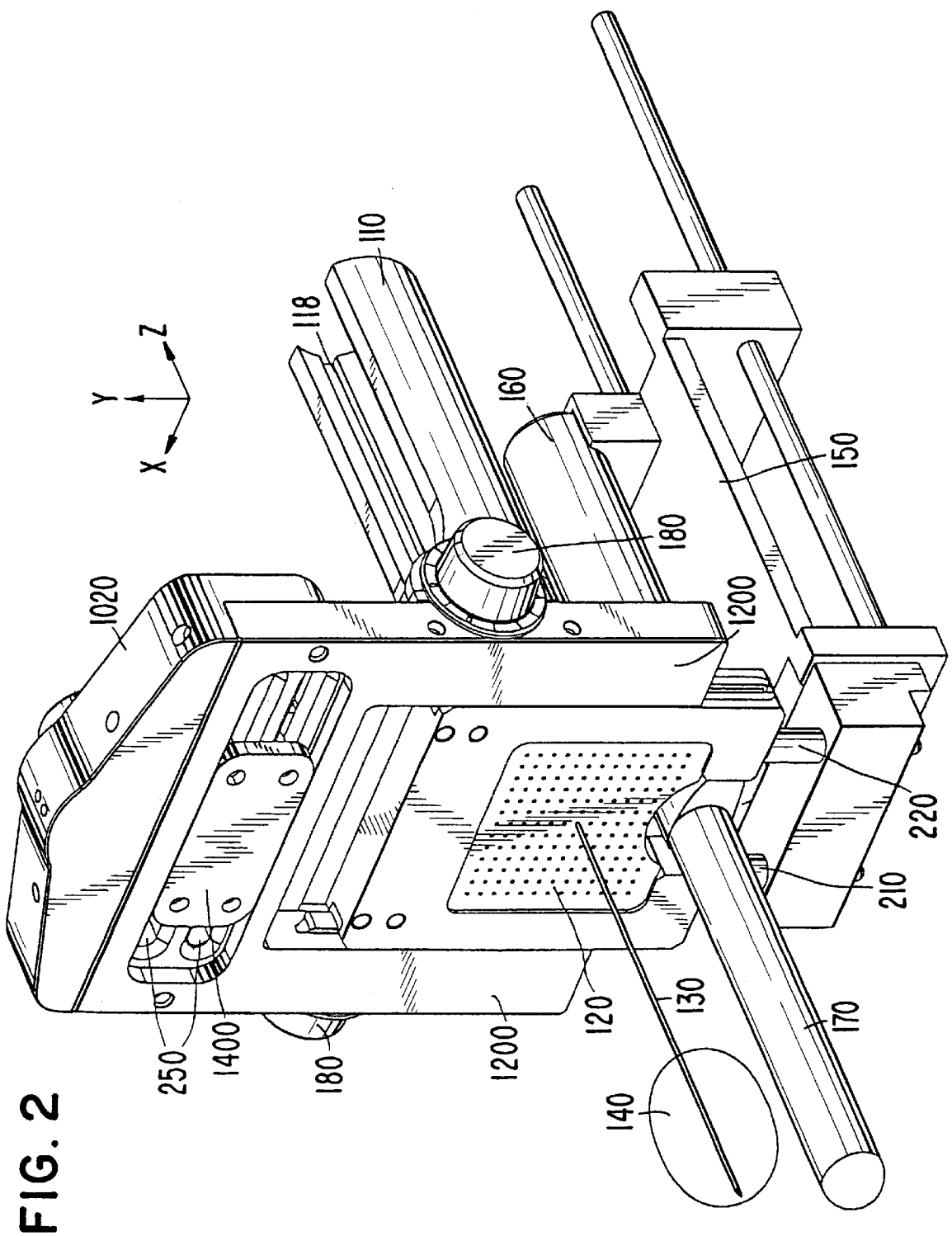
FIG. 2 shows a back perspective view of the targeting fixture according to the present invention.

The present invention is directed to a targeting fixture for a rid template. FIGS. 1 and 2 respectively show a front perspective view and a rear perspective view of a targeting fixture 100 in accordance with the present invention. The targeting fixture 100 includes a cradle unit 110, which is configured to accept a seed implanting instrument (not shown). The cradle unit 110 includes a track 115 that interfaces with a corresponding track of the seed implanting instrument. The track 115 allows for the seed implanting instrument (also called "medical instrument" herein) to be moved in a z-direction with respect to a grid template 120, and thereby provide inwards or outwards movement of a needle 130 with respect to a patient's prostate gland 140.

Details of a medical instrument which is capable of being coupled to the targeting fixture, or more specifically, to the cradle unit of the targeting fixture 100, is a subject of a first related application entitled "MEDICAL INSTRUMENT", U.S. Provisional Application No. 60/205,053, filed May 18, 2000, which is incorporated in its entirety herein by reference. Details of a seed cartridge that can be fitted into the medical instrument is a subject of a second related application entitled "CARTRIDGE-MOVEABLE SHIELD", U.S. Provisional Application No. 60/205,055, filed May 18, 2000, which is incorporated in its entirety herein by reference. Details of different types of targeting fixtures is the subject of a third related application entitled "TARGETING FIXTURE", U.S. Ser. No. 09/858,657, filed May 17, 2001, which is incorporated in its entirety herein by reference.

The present invention is shown as being coupled to a base unit 150, via two coupling legs 210, 220, as seen best in FIG. 2. The base unit 150 is a conventional device, and includes an ultrasound unit 160 and probe 170, for determining a precise location of the prostate gland 140 within a patient's body.

The cradle unit 110 also includes a slot 118 on both the right the left sidewalls of the cradle unit 110, whereby the seed implantation device can be placed therein by way of corresponding protrusions on the right and left sides of the seed implantation device. Other ways of fitting the seed implantation device to the cradle unit 110 may be envisioned while remaining within the scope of the invention as described herein.

To develop the pre-plan, the probe 170 is inserted into a patient's anus, in order to obtain a fixed reference for the base unit 150. Ultrasound is provided to the patient by way of the ultrasound unit 160, and as a needle is inserted into and out of the patient's body, the exact location of the prostate gland 140 can be determined.

Unlike the conventional approach, which requires the doctor to physically hold a seed implantation device in place with respect to a needle inserted into the patient by way of a hole on the grid template, the present invention allows for virtually hands-free treatment of a patient, whereby, once the seed implantation device has been inserted into the cradle unit 110 and the proper z-position is determined for starting to implant seeds into a particular position of the patient's prostate gland, the seed implantation device is not removed from the cradle unit 110 until the entire seed implantation procedure is completed.

In particular, the proper z-position of the cradle unit, and hence the seed implantation device, is provided by an indicator on the exterior of the seed implantation device, which informs the doctor as to the precise distance the seed implantation device is with respect to the grid template (or some other reference, such as the patient's skin). A plurality of numeric indicators are preferably provided on the top portion of the seed implantation device, whereby one of the numeric indicators lines up with a tick-mark (not shown) on the top part of the cradle unit 110, in order to inform the doctor as to the current z-position of the seed implantation device. Once the correct z-position has been achieved, by sliding the seed implantation device along the track 115 until the correct numeric indicator for the z-position for an initial seed implanting of the patient is obtained, the seed implanting device is positioned to begin inserting seeds into the patient.

The housing 1200 of the targeting fixture 100 snugly fits around the grid template 120, and has an x-knob 185 and a y-knob 180 provided thereon. In the preferred embodiment, there is an x-knob provided on both sides, but only one is required. Based on the pre-plan, the doctor first places a needle into the proper position on the grid template, such as position "C-5". Then, the doctor sets the x-knob 185 to the "5" position and the y-knob 180 to the "C" position. Once set to their respective positions, the seed implantation device is positioned to be connected to the needle, without any worry about damaging the needle or misaligning any of the elements during the treatment of the patient.

With the x, y and z-positions properly set, one or more seeds can be provided to the patient by way of the seed implantation device. That is, one or more seeds are provided to a particular location of the patient's prostate gland 140 via the needle positioned into hole "C-5" on the grid template 120. For instance, one seed could be implanted at the zero retraction plane, the seed implantation device could then be moved (by way of the track 115 and a corresponding track on the bottom of the seed implantation device) back to a different z-position, another seed could then be inserted into a different depth (but the same axial position) within the patient's prostate gland 140, and so on.

After all of the seeds have been implanted via the needle 130 positioned into hole "C-5" of the grid template 120, the targeting fixture 100 is ready to reposition the seed implantation device without the doctor having to physically handle the seed implantation device. In particular, the cradle unit 110 is moved upwards via hinge unit 220, so that it is placed up and away from the grid template 120. Preferably, when the cradle unit 110 is hinged upwards, the cradle unit 110 is locked into place, so that it would not fall back down to an inadvertent bumping against the targeting fixture 100.

With the cradle unit 110 and seed implantation device within the cradle unit 110 so positioned in an upwards position, the needle 130 can be removed from hole C-5 of the grid template, and a new needle can be inserted into another hole, say hole G-1, of the grid template 120, in order to provide one or more seeds to a different axial location within the patient's prostate gland 140.

With the needle 130 in place within the hole G-1 of the grid template 120, the hinge unit 220 can then be rotated back downwards. Then, the x-knob 185 and the y-knob 180 of the targeting fixture 100 are set to positions "G" and "1", respectively, so that the cradle unit 110, and thus the seed implantation device housed within the cradle unit 110, are axially lined up with the needle 130 positioned within hole G-1 of the grid template 120.

The track 115 of the cradle unit 110 provides for movement of the seed implanting device in a manner that, when one seed is inserted into the patient, the seed implantation device automatically retracts by a fixed amount, so as to place the seed implantation device at a location for a next seed to be inserted into the patient.

The present invention is described with respect to a targeting fixture that includes a grid template 120, where two coupling legs 210, 220 extending from bottom ends of the U-shaped housing 1200 of the targeting fixture 100, are coupled to the base unit 150. Alternatively, the two coupling legs 210, 220 could extend directly from the bottom surface of the grid template 120, so that the-present invention could be configured to couple with a conventional grid template already mounted onto a conventional base unit 150. A conventional grid template includes 13 rows and 13 columns of holes, with a spacing of 5 mm between adjacent holes.

Figure 3:
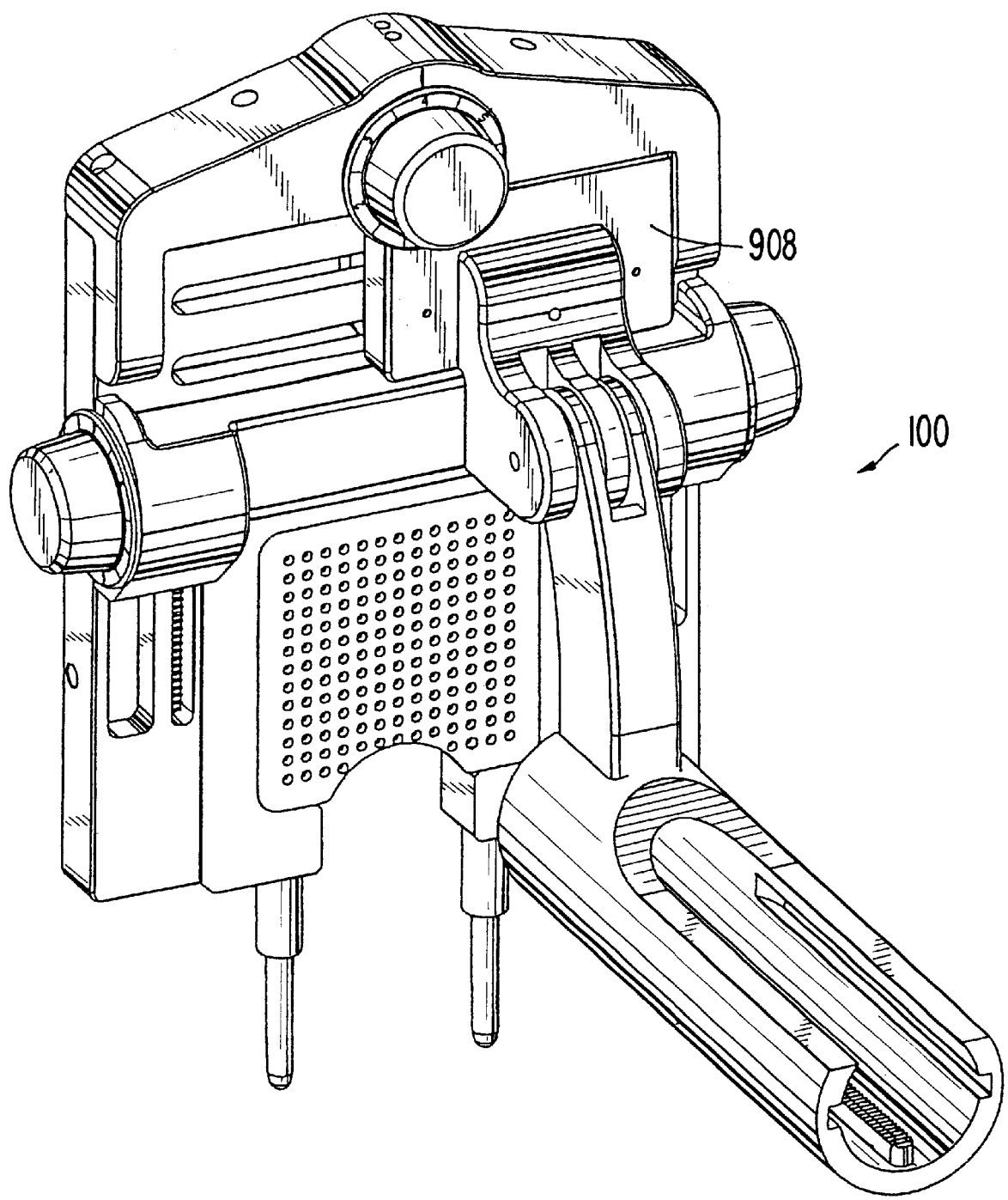
FIG. 3 shows a front perspective view of the targeting fixture by itself, according to the present invention.
Figure 4:
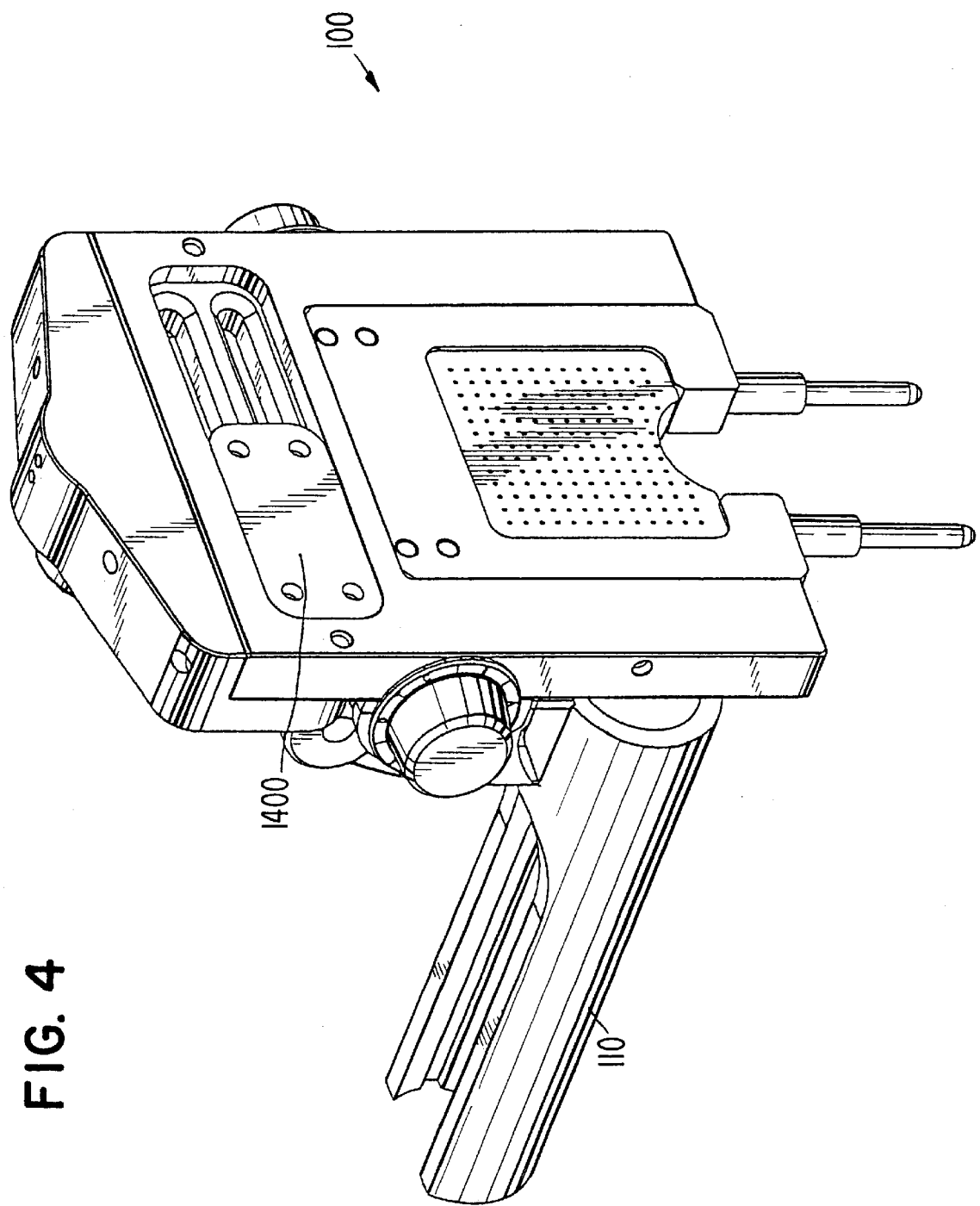
FIG. 4 shows a back perspective view of the targeting fixture by itself, according to the present invention.
Figure 5:
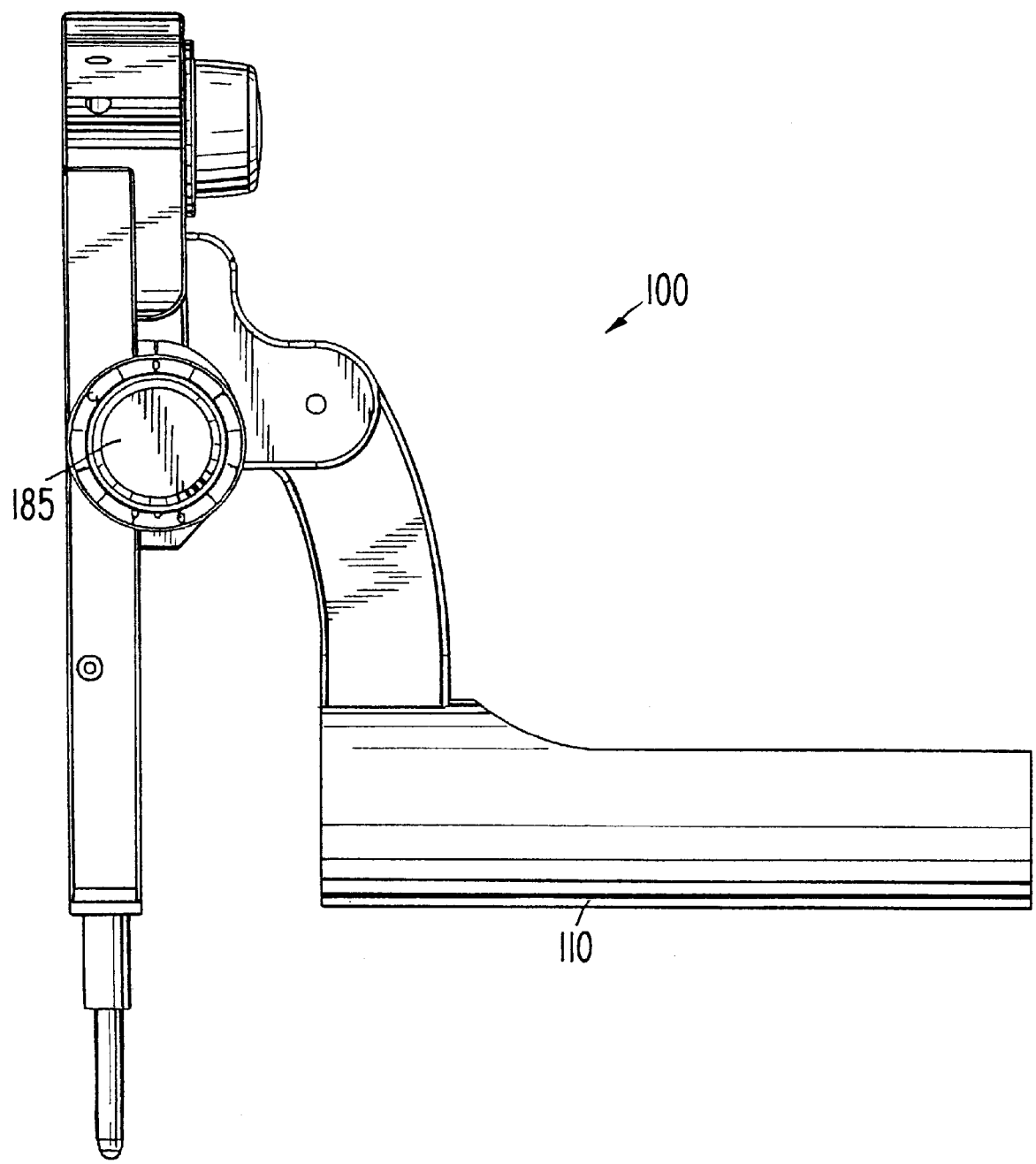
FIG. 5 shows a side view of the targeting fixture, with the y-knob clearly shown, according to the present invention.
Figure 6:
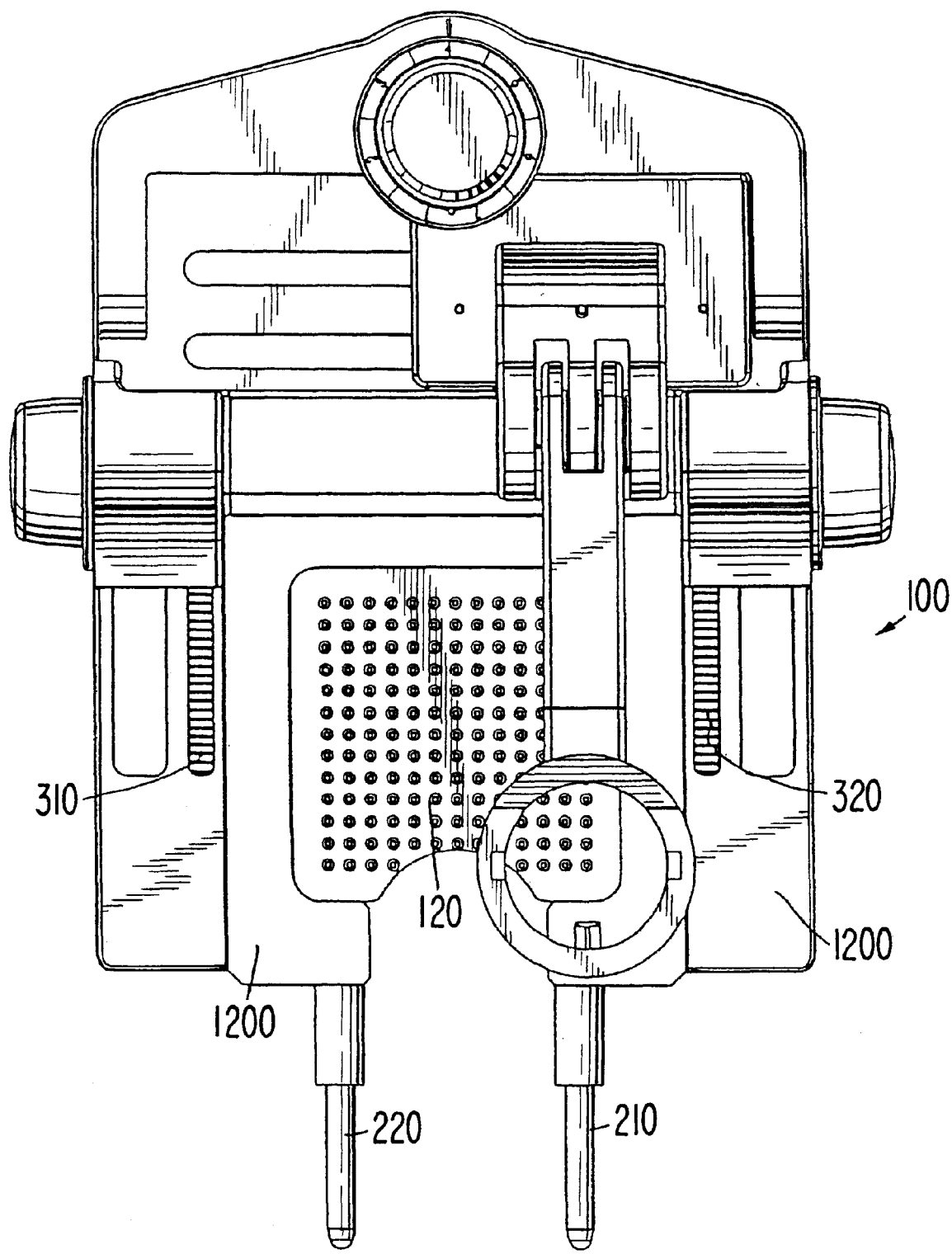
FIG. 6 shows a front view of the targeting fixture, according to the present invention.

FIG. 3 shows a blown-up view of the front of the targeting fixture 100, which shows a rack 310 provided on one side of the housing 1200, to provide for up-and-down (y-direction) movement of the targeting fixture 100, and hence the seed implantation device housed within the cradle unit 110, with respect to the grid template 120. Another rack 320, as shown in FIG. 6, is provided on the opposite side of the housing 1200.

Figure 8:
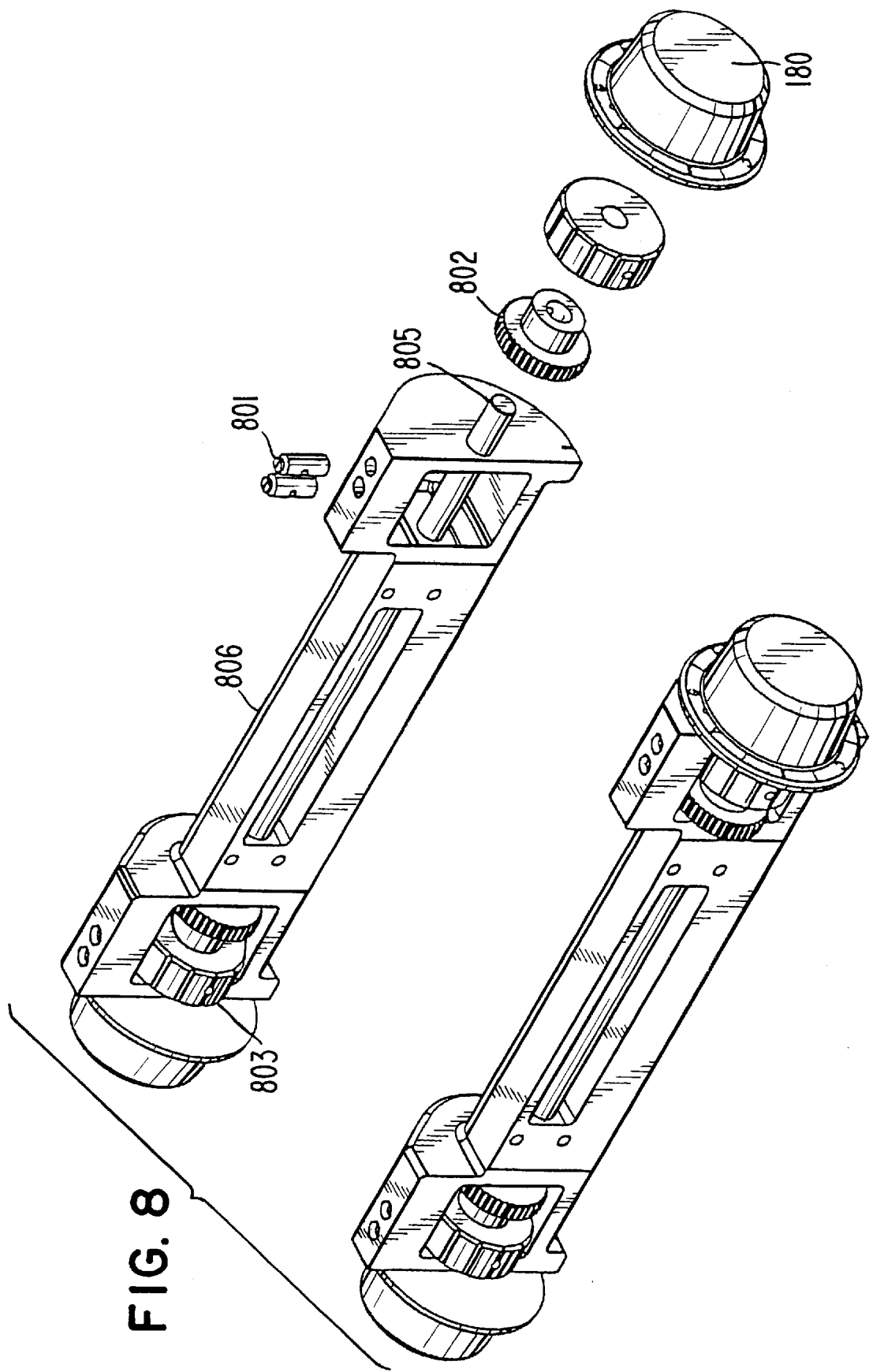
FIG. 8 shows a y-axis carriage adjustment assembly, according to the present invention.

FIG. 8 shows the y-carriage assembly used in the preferred embodiment. Other ways of achieving y-movement may be envisioned while remaining within the scope of the invention as described herein. In FIG. 8, a gear 802 engages the rack 310, with one gear 802 provided for each rack 310, 320. The y-knob 185 is fitted onto the gear 802, where rotation of the y-knob 185 results in rotation of the gear 802, and thus up-and-down movement of the targeting fixture by way of movement of the gears 802 up or down the racks 310, 320. The gears 802 on both sides of the grid template 120 are coupled together by way of a y-shaft 805. Also shown in FIG. 8 are ball spring plungers 801, which are springs with a ball in them. The ball spring plungers 801 fits into slots provided on opposite sides of the housing 1200 surrounding the grid template 120, and they provide a "clicking" sound to let a user know when they have moved to a particular y-position. The ball spring plungers 801 are preferably hard, stainless steel parts, which are very wear-resistant.

Figure 7:
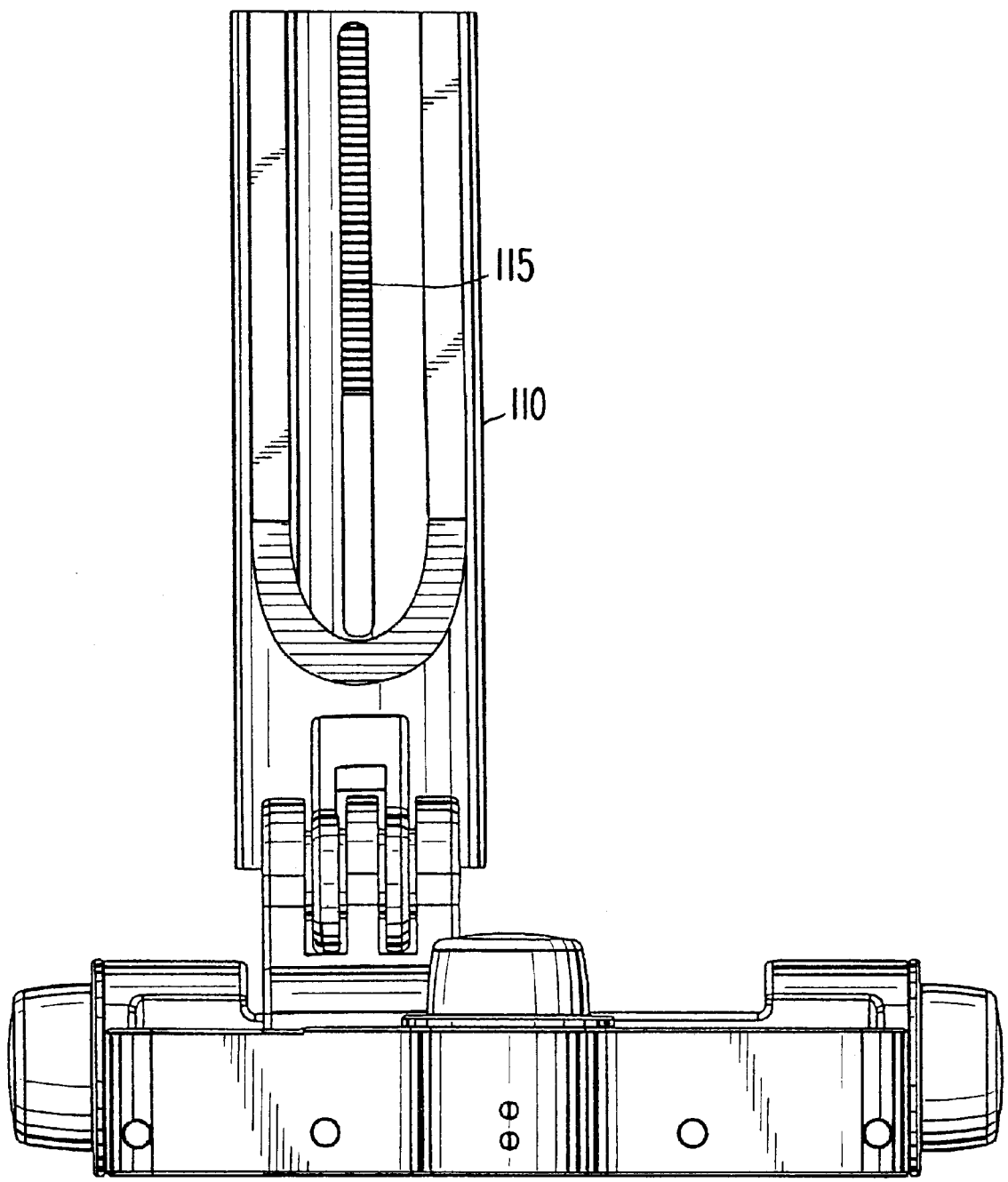
FIG. 7 shows a top view of the targeting fixture, according to the present invention.
Figure 9:
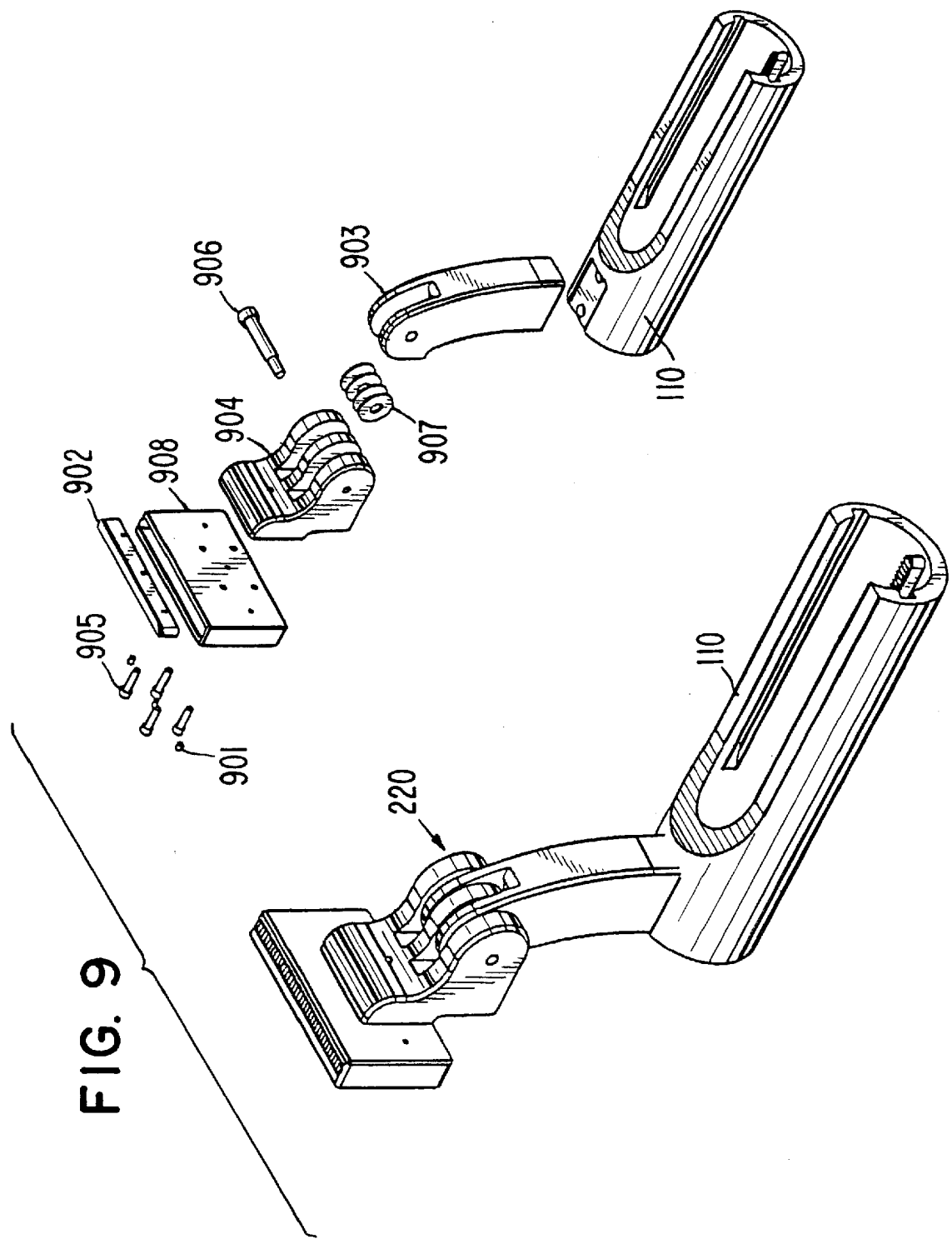
FIG. 9 shows a pivot, or hinge arm assembly, according to the present invention.

FIG. 9 shows the components making up the hinge unit 220, and FIG. 7 shows the hinge unit 220 (and the track 115 of the cradle unit 110) when viewed from above the targeting fixture 100. The hinge unit 220 includes a pivot arm 903, which mounts to the cradle unit 110. The hinge unit 220 also includes a plurality of washers 907, a shoulder screw 906, and a pivot mount 904. The shoulder screw 906 is fitted into the pivot mount 904, with one washer 907 provided between each of the three legs of the pivot mount 904. The pivot mount 904 is mounted onto an x-axis slide carriage assembly 908. The disposition of the slide carriage assembly 908 in the targeting fixture 100 can be seen in FIG. 2. A pitch rack 902 is provided at a top portion of the x-axis slide carriage assembly 908, to provide the mechanism for the x-axis slide carriage assembly 908 to move either left or right within the slots 250, as seen in FIGS. 2 and 7. The hinge unit 220 provides sufficient tension so that the cradle unit 110, with a seed implanting unit held therein, will not fall downwards unless a relatively strong amount of force is provided in a downwards direction with respect to the pivot mount 904.

The hinge unit 220 can alternatively be provided with a ratcheting mechanism so as to ratchet the hinge unit 220 upwards to a fully-upwards position. At the fully-upwards position, a release can then be engaged in order to set the hinge unit 220 back down so that it can be re-engaged with a needle.

Figure 10:
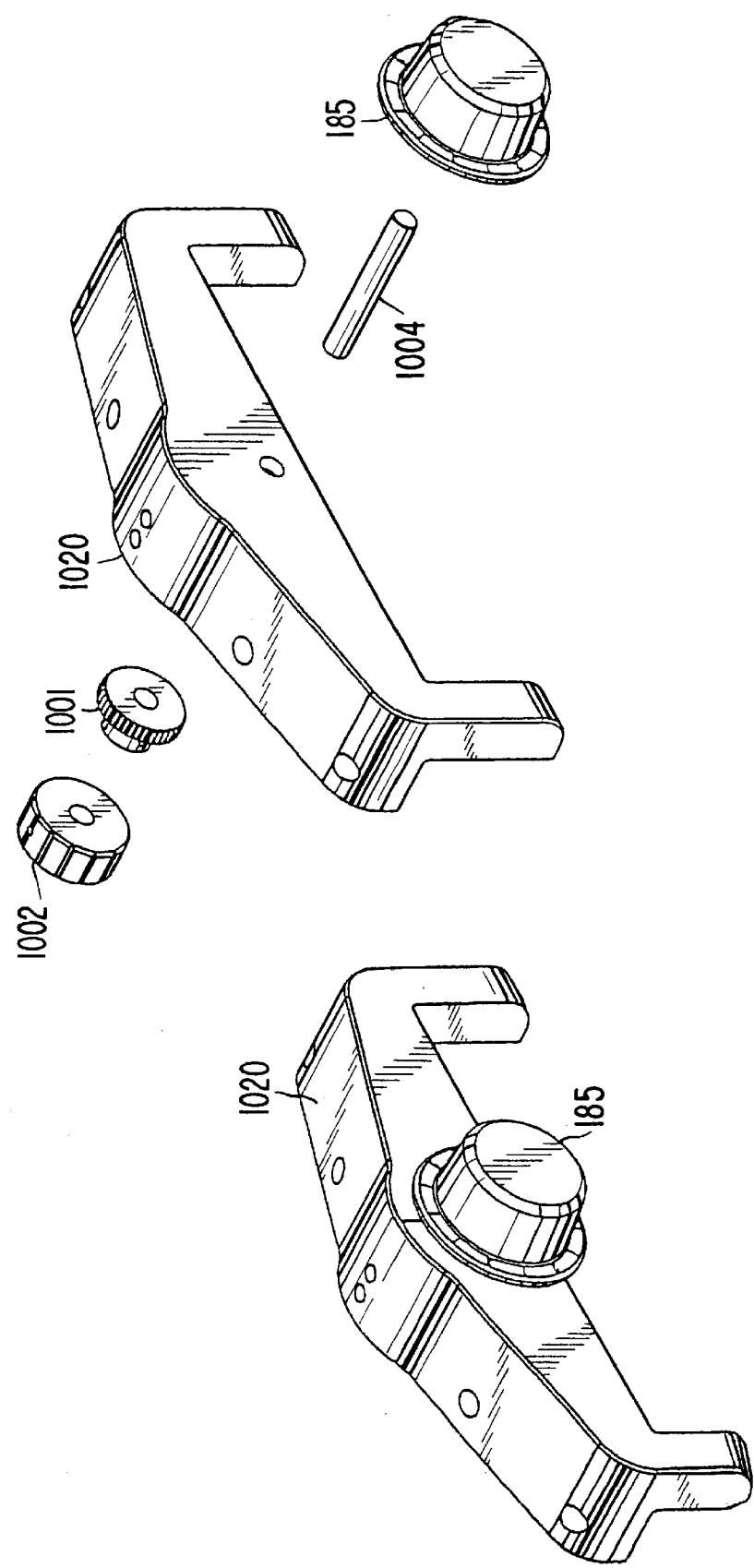
FIG. 10 shows a top housing unit of the targeting fixture, according to the present invention.
Figure 11D:
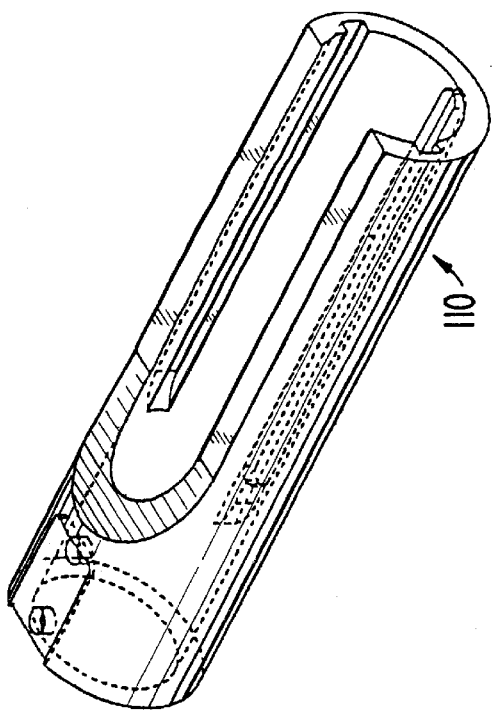
FIGS. 11A–D show different views of the cradle unit, according to the present invention.
Figure 11C:
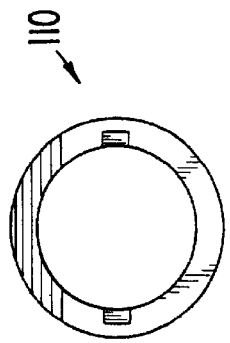
Figure 11A:
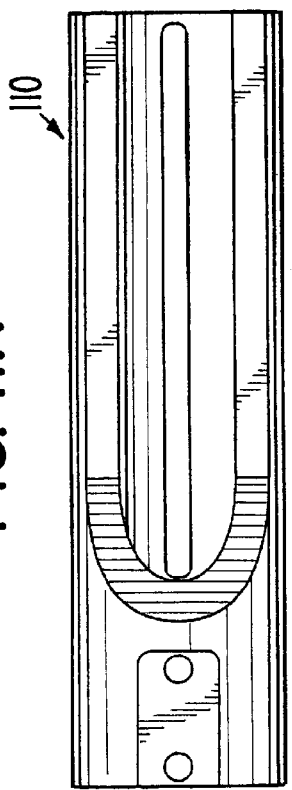
Figure 11B:
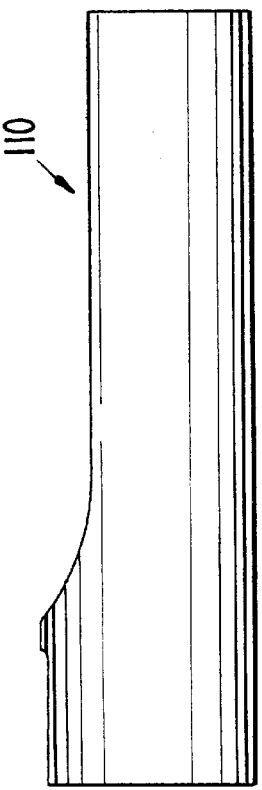
Figure 12D:
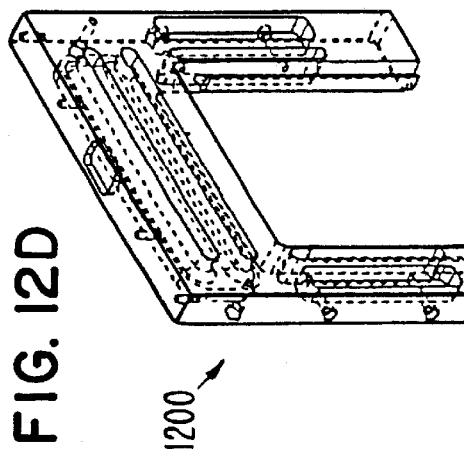
FIGS. 12A–D show different views of the U-shaped housing structure that is adapted to couple to a grid template, according to the present invention.
Figure 12C:
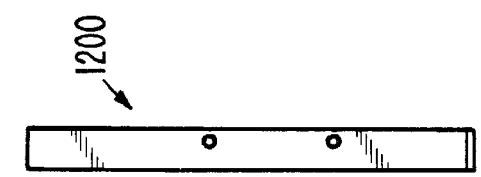
Figure 12A:
Figure 12B:
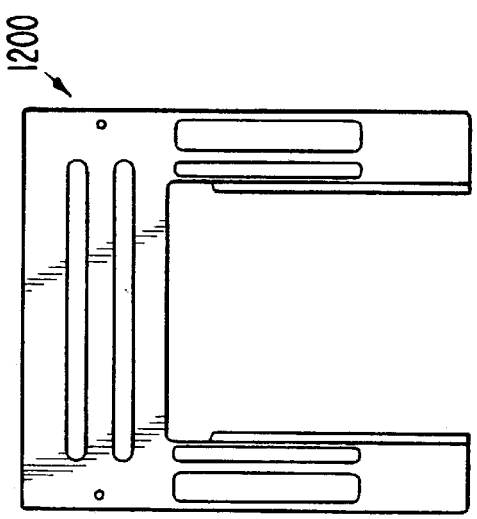

FIG. 10 shows the components making up the x-axis knob assembly. The x-axis knob assembly includes a top housing 1020 that is fitted onto the U-shaped housing structure 1200, the x-axis knob 185, a gear 1001, an indexer 1002, and an x-shaft 1004. When the x-axis knob 185 is turned, this results in the gear 1001 turning as well, which moves along the rack 902 to cause the x-axis assembly, and thus the cradle unit 110 of the targeting fixture 100, to move in an x-direction with respect to the grid template 120.

FIGS. 11A–D show different views of the cradle unit 110. FIGS. 12A–D show different views of the U-shaped housing structure 1200 that surrounds the grid template 120. The U-shaped housing structure 1200 includes slots provided for allowing x-direction and y-direction movement of the targeting fixture 100 with respect to the grid template 120.

Figure 13A:
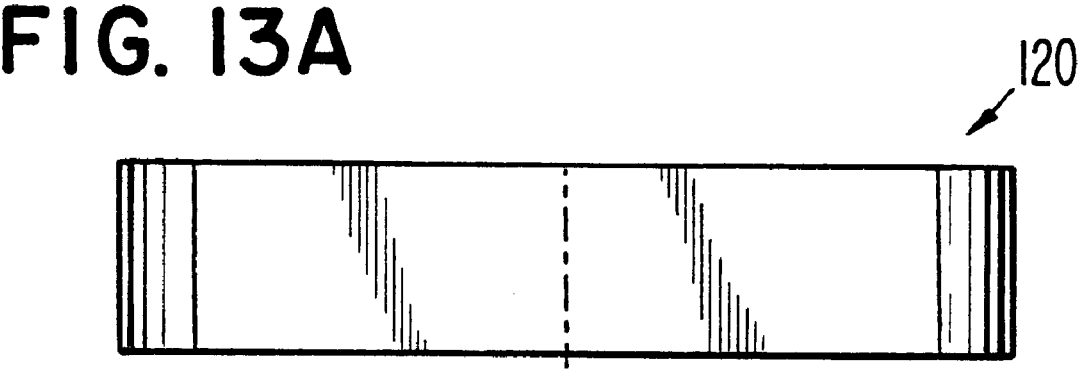
FIGS. 13A and 13B show different views of a grid template that can be used with the targeting fixture, according to the present invention.
Figure 13B:
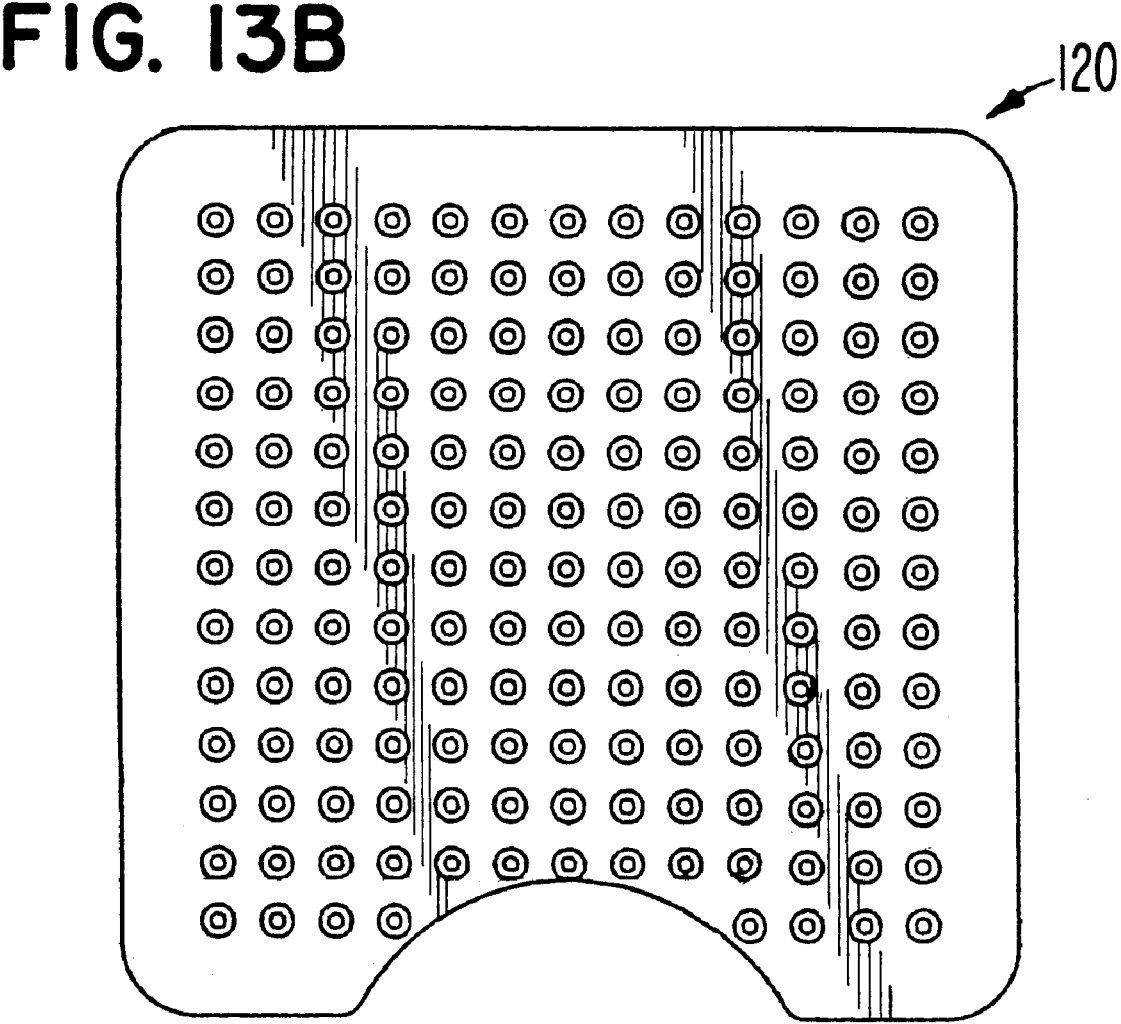
Figure 14D:
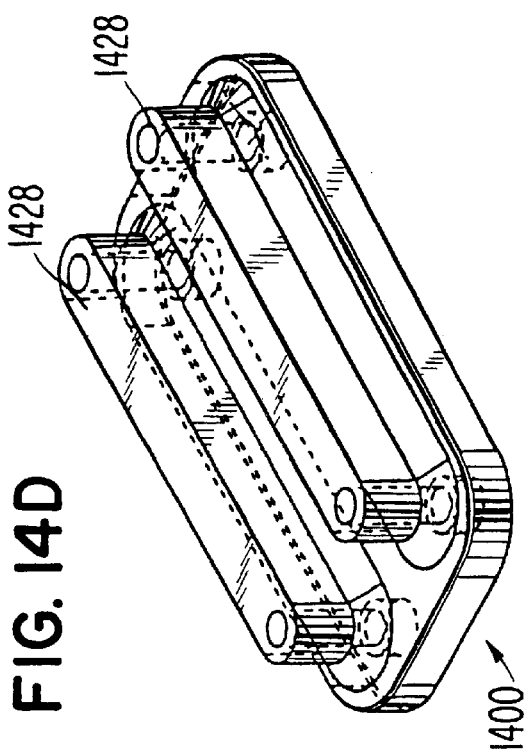
FIGS. 14A–D show different views of an x-slider back plate, according to the present invention.
Figure 14C:
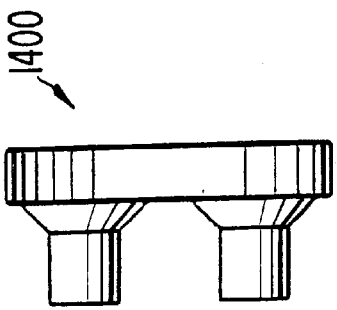
Figure 14A:
Figure 14B:
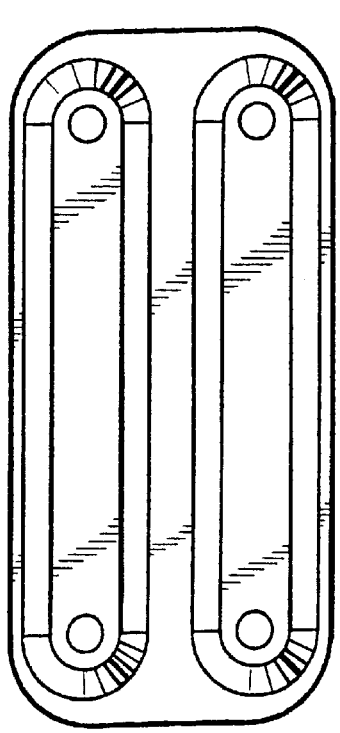
Figure 15C:
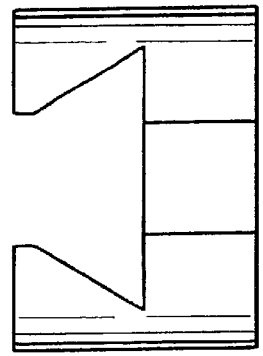
FIGS. 15A–D show different views of a dovetail track, according to the present invention.
Figure 15D:
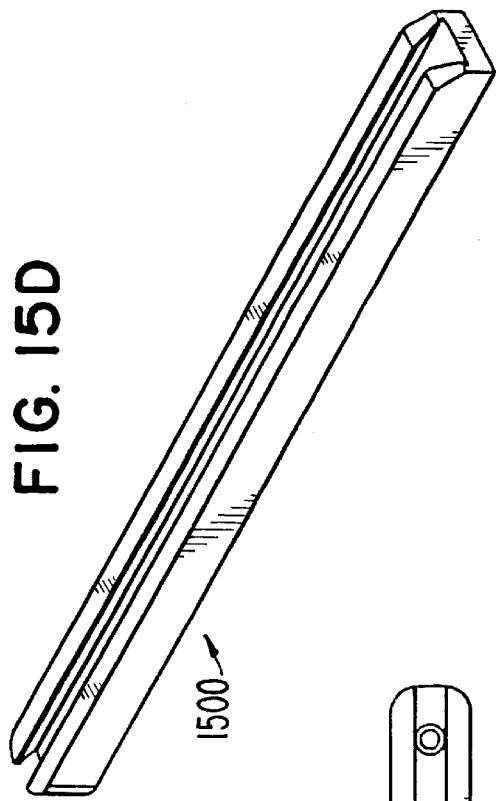
Figure 15A:
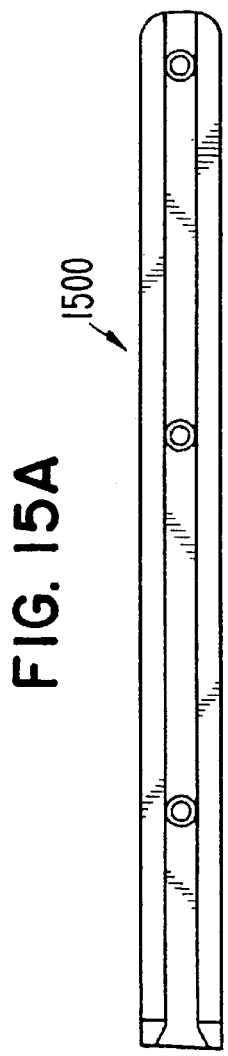
Figure 15B:
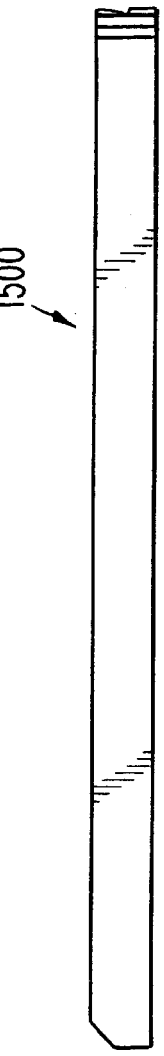

FIGS. 13A and 13B show in detail a grid template that can be used with the present invention. FIGS. 14A–D show different views of an x-slider back plate 1400. The x-slider back plate 1400 includes two raised regions 1410, 1420, which are fitted onto the slots 250 and which move in a left-right direction on the slots 250, based on actuation of the x-knob 180. The x-slider back plate 1400 is coupled to an x-axis slide carriage housing (see FIG. 16) by way of four screws in the preferred embodiment.

FIGS. 15A–D show different views of a dovetail track 1500. The dovetail track 1500 holds the track for x-axis movement in place. FIGS. 16A–E show different views of an x-axis slide carriage housing 1600, where the dovetail track 1500 and x-axis track are fitted into the top channel of the x-axis slide carriage housing 1600, and where the x-slider back plate 1400 is fitted to a back side (see FIG. 2) of the x-axis slide carriage housing 1600.

In the present invention, the grid template 120 is removable from the housing surrounding the grid template 120, so that the grid template 120 may be sterilized, and then reattached to the targeting fixture 100 for reuse.

While the above components are described with respect to the preferred embodiment, other similar types of components may be utilized, while remaining within the spirit and scope of the present invention, as exemplified by the claims.

What is claimed is:

1. A targeting fixture for a grid template, comprising:
   a housing that includes an opening within which the grid template is coupled thereto;
   a cradle unit that is configured to receive a seed implanting device;
   a hinge unit that hingedly connects the cradle unit to the housing; and
   an x-y movement unit that provides at least one of x-direction and y-direction movement of the cradle unit with respect to the grid template.

2. The targeting fixture according to claim 1, wherein the housing includes a mounting element that is configured to mount to a base unit.

3. The targeting fixture according to claim 1, wherein the x-y movement unit comprises:
- a first gear/rack unit that is coupled to a vertical slot in the housing;
- a y-axis knob that is adapted to be turned so as to move the cradle unit in a y-axis direction via the first gear/rack unit;
- a second gear/rack unit that is coupled to a horizontal slot in the housing; and
- an x-axis knob that is adapted to be turned so as to move the cradle unit in an x-axis direction via the second gear/rack unit.

4. The targeting fixture according to claim 1, wherein the hinge unit is configured to be moved upwards in order to move the seed implanting device away from the grid template to allow the seed implanting device to be coupled to a needle positioned at a different location on the grid template than before.

* * * * *